United States Patent [19]

Cousse et al.

[11] 4,098,879
[45] Jul. 4, 1978

[54] N-ALKYL-3-PYRIDINIUM-METHANOL FLUORIDES AND DERIVATIVES THEREOF

[75] Inventors: Henri Cousse; Gilbert Mouzin; Jean-Claude Vezin; Lucien Dussourd d'Hinterland; Jacques Dubois, all of Castres, France

[73] Assignee: Pierre Fabre S.A., Paris, France

[21] Appl. No.: 756,016

[22] Filed: Jan. 3, 1977

[51] Int. Cl.² .................. C07D 213/30; A61K 7/18
[52] U.S. Cl. .................. 424/52; 260/295.5 R; 260/295.5 A; 260/297 R; 544/124
[58] Field of Search ............. 260/297 R; 424/52, 48

[56] References Cited

U.S. PATENT DOCUMENTS 3,914,406  10/1975  Yankell .................. 424/52

FOREIGN PATENT DOCUMENTS 673,101  10/1963  Canada .................. 424/52

OTHER PUBLICATIONS

Karrer, Organic Chemistry, 4th Eng. Ed., p. 928, Elsevier Pub. (NY) 1950.

*Primary Examiner*—Alan L. Rotman
*Attorney, Agent, or Firm*—Gordon W. Hueschen

[57] ABSTRACT

The present invention relates to new chemical compounds which can be used as inhibitors of dental plaque, and orally-acceptable compositions thereof, combinations thereof with known compounds having an inhibitory action on the formation of dental plaque, such as biguanidines, and method of treating therewith for the prevention of dental plaque or tartar and dental caries.

The new compounds have the general formula

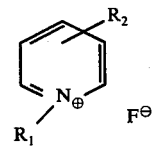

in which
 $R_1$ = H or alkyl
 $R_2$ = $CH_2OH$, alkyl carboxylate,

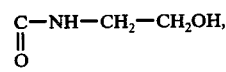

or 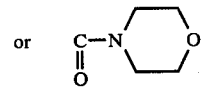

and
 $R_2$ is in 2 or 3 position.

Compositions containing these active principles are useful in particular in the preventive treatment of periodontopathies and odontopathies and in the field of oral-dental hygiene.

23 Claims, No Drawings

N-ALKYL-3-PYRIDINIUM-METHANOL FLUORIDES AND DERIVATIVES THEREOF

BACKGROUND OF THE INVENTION

1. Field of the Invention

Certain novel pyridine compounds and fluoride salts thereof; antiplaque, anticaries and antiperiodontitis compounds; oral and dental hygiene compositions thereof, method of treating therewith, and combinations with known antiplaque compounds such as biguanidines.

2. Prior Art

The oral diseases periodontitis and dental caries are plaque-related problems of a complex nature and origin, which have until the present been most successfully treated or obviated by the mechanical removal of plaque, since the chemical approach to plaque inhibition has not been successful. The present invention, however, provides compounds having relatively low toxicity and which have been shown to be effective for the inhibition of dental plaque and, accordingly, also for the inhibition of dental caries and periodontitis, which problems or ailments are caused by undue buildup of dental plaque and resulting complications.

Since the appearance of the work of Muhleman et al. (Helv. odontol. Acta, 1957), concerning the role of fluorides in the prevention of dental caries, many authors have experimented on amine fluorides or inorganic fluorides.

In general, the complexes recommended are unstable and are deactivated by rapid hydrolysis; this is true of tin fluoride. The organic fluorides are frequently less active, since the ionization constant is low.

All established more or less useful compounds of the prior art have been found to be characterized by serious shortcomings and/or side effects, and there exists a clear and ever-growing demand for more specific and advantageous compounds or treatments in this activity and utility area, especially for antiplaque, anticaries, and anti-periodontitis products and methods. The fulfillment of this demand is one of the objects of the present invention, as will become more fully apparent hereinafter.

The new compounds which are the object of the invention have the advantage of being good carriers of fluorine which have the following properties:
fluorides stable in aqueous solution
high ionization constant
nontoxic organic molecule
and in particular of combining the action of fluorine in the prevention of dental caries with a tonifying effect on the gums and a power of inhibition with respect to the formation of dental plaque.

This is the first time that these three beneficial actions are combined in the same molecule.

SUMMARY OF THE INVENTION

This invention relates to novel pyridine compounds, fluoride salts thereof, orally-acceptable compositions containing the same, a method of using the same for their antiplaque or anticaries properties, and combinations with known antiplaque compounds such as biguanidines.

OBJECTS

It is an object of the present invention to provide certain compounds and fluorides thereof, which are useful in the chemical inhibition of dental plaque and resulting problems or ailments, a process for producing the same, orally-acceptable compositions thereof, a method of treating therewith, and combinations with known antiplaque compounds such as biguanidines. Additional objects will become apparent hereinafter and still other objects will be obvious to one skilled in the art.

THE INVENTION

The present invention, made at the Pierre Fabre Research Center, concerns new chemical compounds and their use in therapy. They may be used in particular for the prevention and treatment of periodontopathies, caries, and dental plaque.

These new chemical compounds have the general formula

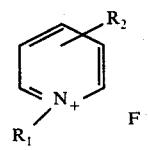   A.

in which:
$R_1$ = H, alkyl
$R_2$ = $CH_2$—OH, alkyl carboxylate,

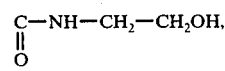

or 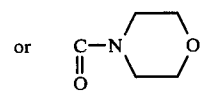

and $R_2$ is in the 2 or 3 position.

The $R_1$ and alkyl carboxylate "alkyl" groups are, independently, an alkyl group, straight or branched, having one to twenty carbon atoms, inclusive, and is preferably an alkyl group, straight or branched, of no more than twelve carbon atoms, but especially such alkyl groups having one to eight carbon atoms, inclusive, including such usual and representative groups as methyl, ethyl, propyl, isopropyl, butyl, isobutyl, sec. butyl, tert. butyl, amyl, hexyl, heptyl, octyl, decyl, dodecyl, octadecyl, nonadecyl, et cetera, as well as corresponding unsaturated, doubly unsaturated, and triply unsaturated radicals, e.g., alkynl, alkenyl, and alkadienyl radicals.

These novel compounds of Formula A have valuable pharmacological properties, especially as inhibitors of dental plaque as further elucidated hereinafter, which makes them useful not only as antiplaque, but also as anticaries and anti-periodontitis, products.

DETAILED DESCRIPTION OF THE INVENTION

The following Examples are given by way of illustration only and are not to be construed as limiting.

3-pyridyl methanol hydrofluoride (product I)

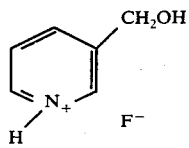

To a methanolic solution of 3-pyridyl methanol add the stoichiometric quantity of hydrofluoric acid in 40% aqueous solution.

Heat the reaction mixture to 60° C. A homogeneous solution is obtained.

The solvents are evaporated to dryness; the 3-pyridyl methanol hydrofluoride is obtained quantitatively.

Empirical formula: $C_6H_8FNO$
Molecular weight: 129.13
Translucent oil
Fluorine content: 14.71
Index of refraction: $n_D^{21} = 1.5010$
Very soluble in water.
pH of 20% aqueous solution: 3.7.

N-hydroxy ethyl nicotinamide hydrofluoride (product II)

Methyl nicotinate is treated with an excess of ethanolamine, the reaction mixture is heated so as to distill the methanol as it is formed.

The N-hydroxy ethyl nicotinamide thus obtained is treated with a 40% aqueous solution of hydrofluoric acid to produce the derivative

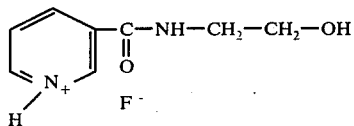

Empirical formula: $C_8H_{11}FN_2O_2$
Molecular Weight: 186.19
Organoleptic characteristics: thick yellow oil
Solubility characteristics: soluble in water
Fluorine content: 10.20%
pH of 20% aqueous solution: 3.1

Ethyl 3-nicotinate hydrofluoride (product III)

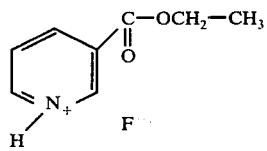

Empirical formula: $C_8H_{10}FNO_2$
Molecular weight: 171.17
Organoleptic characteristics: translucent oil
Index of refraction: $n_D^{22} = 1.4811$
Solubility characteristics: soluble in water
Fluorine content: 11.10%
pH of a 20% aqueous solution: 2.5
Absorption band: $\nu_{C=O}$ at 1730 cm$^{-1}$
Salification band at 2500 cm$^{-1}$ This compound was obtained by: Treatment of ethyl-3-nicotinate with a solution of fluorhydric acid in a stoichiometric quantity.

Compounds wherein the ethyl group is replaced by another alkyl group, such as methyl, octyl, or dodecyl, or octadecyl are prepared in the same manner, namely by: Treatment of the nicotinic esters with a solution of fluorhydric acid in stoichiometric quantity.

N-dodecyl 3-pyridyl methanol fluoride (IV)

To an ethanolic solution of 3-pyridyl methanol there is added a stoichiometric amount of dodecyl fluoride.

The reaction mixture is heated under reflux for 8 hours.

After evaporation of the solvent to dryness, there is quantitatively recovered the compound:

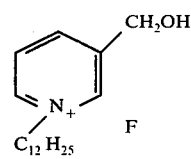

Empirical formula: $C_{18}H_{32}NOF$

Compounds wherein the dodecyl group is replaced by another alkyl group, e.g., methyl, ethyl, octyl, or octadecyl, are obtained in the same manner using the selected alkyl fluoride instead of dodecyl fluoride.

There were also obtained:
3-nicotinoyl morpholine hydrofluoride:

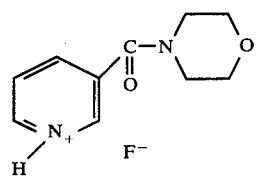

(V)

2-pyridyl methanol hydrofluoride

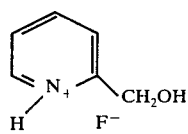

(VI)

These compounds were obtained, respectively, by:
(V) Treatment of 3-nicotinoyl morpholine with a solution of fluorhydric acid in stoichiometric quantity.
(VI) Treatment of 2-pyridyl methanol with a solution of fluorhydric acid in stoichiometric quantiy.
methyl 3-nicotinate hydrofluoride

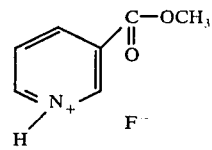

(VII)

This compound was obtained by: Treatment of methyl-3-nicotinate with a solution of fluorhydric acid in stoichiometric quantity.

Compounds wherein the methyl radical of the methoxy group is replaced by other alkyl groups such as ethyl, octyl, dodecyl, and octadecyl are prepared in the same manner, namely by: Treatment of the nicotinic esters with a solution of fluorhydric acid in stoichiometric quantity.

EXPERIMENTS

A — Pharmacology (a) Protective action on the tooth enamel

The properties were studied in vitro in accordance with the ESR (Enamel Solubility Reduction) tests.

Groups of sound human teeth were treated, after protecting the roots with acid-resistant varnish, by aqueous solutions of amine fluorides and hydrofluorides which form the object of the invention, at 37° C. Control teeth were treated with sodium chloride solutions. The teeth were then decalcified with a phthalate buffer solution of a pH of 4.

The results are evaluated by complexometric determination of the calcium by the method of SCHWARZENBACH, and colorimetric determination of the phosphorus by the method of FISKE and SUBVAROW, respectively published at: "Complexometric Titratocus 2nd ed. Methuen London — 1969, pp. 165-70"; "Complexometric Titratocus — Methuen Ltd. London — 1957", and "J. Biol. Chem. 66 - 375 (1925)", respectively.

The concentration of active fluorides, the contact time, and the pH were varied in turn.

The comparison of the amounts of calcium and phosphorus removed in the case of the treated teeth and in the case of the control teeth makes it possible to evaluate the enamel protective action (Tables I and II):

TABLE I

| Determination of calcium | | |
|---|---|---|
| | Amount of calcium extracted* | % protection |
| Product I | 0.18 mg | 95.5 |
| Product II | 0.19 mg | 95.3 |
| Product III | 0.11 mg | 97.2 |
| Control | 4.03 mg | 0 |

*Average of 14 measurements on different groups of teeth

Table II

| Determination of phosphorus | | |
|---|---|---|
| | Amount of P extracted* | % protection |
| Product I | 0.17 | 93.3 |
| Product II | 0.20 | 92.1 |
| Product III | 0.14 | 94.5 |
| Control | 2.55 | 0 |

*Average of 14 measurements on different groups of teeth (b) Inhibiting action on dental plaque in vitro The in vitro activity was measured by adaptation of the method of OLSON, BLEI WEIS and SMALL ("Infection and Immunity", 1972, 5, 419) in which the plaque is obtained on the wall of test tubes and its amount determined spectrophotometrically in $10^{-2}$ optical density at 540 nanometers.

The reading is effected after washing the tubes with water, detaching the plaque with 20 ml of 0.5 N caustic soda solution; the results are compared with the culture control tubes (T) in 5% saccharose Jordan medium without inhibiting substance.

| | 15 μ g/ml OD (optical density) | % inhibition | 7 μ g/ml OD (optical density) | % inhibition |
|---|---|---|---|---|
| Control | 105 | 0 | 105 | 0 |
| Product I | 0 | 100% | 10 | 80% |
| Product II | 15 | 85% | 70 | 30% |
| Product III | 0 | 100% | 30 | 70% |

(c) Bactericidal activity

The minimal bactericidal concentrations (MBC) were determined for different strains of microbes; the results are expressed in μ g/ml.

| Strain CMB | Salmonella brancaster | Streptococci | Hafnia | Citrobacter | Achromobacter |
|---|---|---|---|---|---|
| Product I | 15 | 15 | 30 | 15 | 7 |
| Product II | 30 | 30 | 60 | 30 | 30 |
| Product III | 30 | 15 | 30 | 15 | 15 |

The minimum concentrations for the inhibition of plaque are of the same order as the minimum bactericidal concentrations for streptococcus mutans, namely 15 μg/ml for products I and III; derivative II is on the whole less active.

(d) Tolerance in vivo

Skin tolerance

The tolerance was determined for each derivative on five adult albino guinea pigs. The application of the undiluted products three times a week for 2 weeks on the previously shaven side of the animal does not cause any appreciable skin reaction.

Ocular tolerance

The ocular tolerance was determined on albino rabbits and on mice. After instillation into the conjunctival eye sac of two drops of solution (concentration varying from 1 to 5%) the behavior of the animal is observed for three minutes for all the compounds tested; no difference was observed as compared with a group of control animals.

Epicutaneous tolerance

Epicutaneous tests were carried out on rabbits of New Zealand race. After having shaven the sides of the animal, scrapings were effected of the stratum corneum. The results evaluated on basis of Draize's scale showed that for most of the products the index of irritation is very low.

Intra-dermic tolerance

The intra-dermic tests were carried out by injection of 0.1 ml of 1% solution of product in olive oil. The injections were repeated every day on the sides of previously shaven guinea pigs. After 2 weeks of rest, a similar injection was made above the preceding zone of injection; the extent, diameter, and color of the reactions were compared. All of the observations effected show that there is no primary irritation of sensitization.

B — Therapeutic and Cosmetic Uses

In view of the excellent tolerance of these new chemical compounds, clinical tests were carried out on volunteers. The results were very encouraging and these experiments made it possible to objectively establish the effectiveness of these new active principles.

They are endowed with inhibiting properties with respect to dental plaque in vitro, acting to protect the enamel and to tone the gums by improvement of the blood circulation. They have therefore been used in the field of dentistry, particularly in the preventive and curative treatment of periodontopathies. The active principles have been presented in suitable pharmaceutical forms such as dentifrices, gingival pastes, chewing gum, sucking pastilles, mouthwashes, etc.

Despite their broad spectrum of activity and their action at all levels (plaque, enamel, gums) these active principles can be used in combination.

Experiments were also carried out with respect to the use of the new chemical compounds of the invention in dentifrice preparations exerting an inhibiting action on dental plaque and in dentifrice preparations useful in the prevention of dental diseases, particularly caries.

Compounds or products IV through VII, upon testing, exhibit antiplaque protective action on tooth enamel in the same manner as set forth in the foregoing for compounds I through III.

The foregoing description concerns:

1. New chemical compounds having the general formula

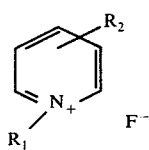

in which
$R_1$ = H, alkyl
$R_2$ = $CH_2$—OH, alkyl carboxylate,

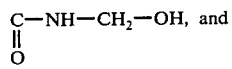

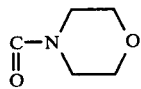

and $R_2$ is in 2 or 3 position.

These chemical compounds have the advantage of combining the action of fluorine for the prevention of dental caries with a tonifying effect on the gums and a power of inhibition with respect to the formation of dental plaque. They are useful in the preventive and curative treatment of ailments of the mouth, the periodontium, and the teeth.

2. Pharmaceutical and cosmetic preparations containing these active principles, alone or in combination.

It has now been shown that the activity of these active principles can be potentiated if they are associated with other active principles having an action preventing dental plaque, such as the biguanides and benzethonium hydrochloride. The latter have been described in U.S. Pat. Nos. 2,684,924, 2,830,006, 2,863,019 and 2,990,425.

It is known that these biguanides which have an inhibiting action on the formation of dental plaque can, under special conditions of use and concentration, cause the browning of the teeth, which limits the field of use thereof.

The object of the present discovery, developed at the Pierre Fabre Research Center, is therefore to improve the preparations previously disclosed herein by the addition of biguanidine derivatives, such as chlorhexidine and its salts as well as benzethonium hydrochloride.

This improvement is characterized by the potentiation effect between the activities of the agents constituting these combinations, as will be shown hereinafter. One immediate advantage is that it makes it possible to decrease the doses of active principles. Thus, with the doses used within the scope of the new combinations, the browning effect of the biguanidines on the teeth is suppressed.

The new combinations concern in particular "oral compositions", this expression designating products which are normally retained for a certain period of time in the oral cavity and which come into contact with all of the surfaces of the teeth. These products are not deliberately swallowed. They are in the form of dentifrices, mouthwashes, prophylactic pastes, topical solutions, and chewing gums.

The excipients are defined in order to optimalize the activity of the active principles, under conditions of maximum stability. In this connection it has been shown that the protection of teeth, as determined by the E.S.R. technique (Enamel Solubility Reduction technique) is practically zero if the fluorinated active principles are applied at a pH $\geq$ 8.

This point was furthermore emphasized by D. COMAR at the convention on the applications of fluorine held in Moscow in 1974. The amount of fluorine fixed as a function of the pH has been the object of a study by Y. ERICSSON (published in Acta. Odont. Scand. at 1958 b - 16, p. 127–141).

The examples of compositions described below have been developed by taking these requirements into account so as to assure optimalization of the inhibiting activity on the formation of dental plaque and on the protection of the enamel. The dentifrice compositions have a pH close to 5.

Example 1

| Toothpaste: | |
|---|---|
| 3-pyridyl methanol hydrofluoride | 0.1 to 2% |
| chlorhexidine hydrochloride | 0.01 to 0.1% |
| glycerin | 5 to 30% |
| hydroxy-ethyl cellulose | 2 to 4% |
| sorbitol | 25% |
| sweetener and flavoring | q.s. |

Example 2

| Toothpaste: | |
|---|---|
| ethyl 3-nicotinate hydrofluoride | 0.1 to 2% |
| benzethonium hydrochloride | 0.01 to 0.2% |
| ethylene-oxide/propylene-glycol complex | 4% |
| hydroxy-ethyl cellulose | 2 to 4% |
| sweetener and flavoring | q.s. |

Example 3

| Mouthwash (pH = 5) | |
|---|---|
| ethyl 3-nicotinate hydrofluoride | 0.1 to 2% |
| benzethonium chloride | 0.01 to 0.2% |
| pyrrolidone carboxylic acid | 0.5 to 5% |
| hydroxy-ethyl cellulose | 0.5 to 2% |
| sweetener and flavoring | q.s. |

Example 4

| Dental tooth gel: | |
|---|---|
| ethyl 3-nicotinate hydrofluoride | 0.1 to 2% |
| chlorhexidine bihydrochloride | 0.01 to 0.1% |
| Carbopol 934 | 0.5 to 4% |
| propylene glycol | 1 to 10% |
| ethanol | 1 to 5% |
| ethylene-oxide/polypropylene-glycol complex | 4% |
| sweetener and flavoring | q.s. |

In order to demonstrate the potentiation effect of the chlorhexidine and benzethonium hydrochlorides on the bactericidal and anti-plaque activities of the 3-pyridyl methanol and ethyl nicotinate hydrofluorides, the following tests were carried out:

| | minimum dose inhibiting plaque in vitro |
|---|---|
| Benzethonium hydrochloride | 15.6 μ g/ml |
| Ethyl 3-nicotinate hydrofluoride | 15.6 μ g/ml |
| 20% benzethonium hydrochloride + 80% ethyl 3-nicotinate hydrofluoride | 7.8 μ g/ml (*) |

(*) total weight of the two active principles.

The anti-plaque activity is determined in accordance with the method described by Plissier et al. (Le chirurgien dentiste, October 16, 1974, page 63) and expressed in inhibiting concentration μg/ml of solution.

A very definite potentiation was shown in this test by using the combination of benzethonium + ethyl 3-nicotinate hydrofluoride as compared with each active principle used separately.

The same is true in the case of the combination of chlorhexidine with ethyl 3-nicotinate hydrofluoride.

| | Dose inhibiting plaque in vitro μg/ml |
|---|---|
| Chlorhexidine hydrochloride | 7.80 |
| Ethyl 3-nicotinate hydrofluoride | 15.6 |
| 80% chlorhexidine + 20% ethyl 3-nicotinate hydrofluoride | 3.9 (*) |
| 20% chlorhexidine + 80% ethyl 3-nicotinate hydrofluoride | 7.8 (*) |

(*) total weight of the two active principles

This synergism makes it possible to obtain antiplaque and anticaries compositions which have an activity superior to the compositions at present known.

The galenic forms produced have made it possible to select the excipients and to exclude those which inhibit the effect of the chlorhexidine.

The activity of the fluoride ions was increased by adjusting the pH to the vicinity of 5; all the products capable of forming insoluble complexes of fluorine were discarded (silica, inorganic phosphates, etc.).

Many other salts of chlorhexidine and/or benzethonium besides the hydrochloride are known and may be employed in place of those shown in the foregoing Examples, the exact salt obviously not being critical.

EXPERIMENTS

Using the methods described in the foregoing pages, experiments were carried out on the combinations which form one object of the present invention.

Excellent tolerance was found with respect to the mucous membranes.

These compositions have the properties required for use in the cosmetic field. No browning of the teeth due to biguanidines was noted. On the other hand, there was noted a tropic action at the level of the gums, imputable to the presence of nicotine derivatives and the presence of pyroglutamic acid. The latter was used to acidify the compositions to a pH of 5. It was selected because of its excellent local tolerance and its innocuousness. The results of the clinical experiments are encouraging. There was found substantially increased effectiveness of the pharmaceutical preparations for the prevention of dental diseases, particularly caries and gingivitis caused by dental plaque.

In the field of oral-dental hygiene, the preparations forming an object of the invention have given very satisfactory results. They meet the criteria and standards required for cosmetic oral-dental application, exerting a cleaning action on the teeth and the mucous membranes.

The foregoing composition Examples may also omit the chlorhexidine or benzethonium compound but the amount of remaining active ingredient is then preferably doubled in amount.

In use, the compounds may be employed as chewable or dissolvable tablets in which they are present together with usual orally-acceptable carriers, excipients binders, and the like. For example, tablets may be prepared conventionally by compounding one of the new compounds with customary carriers and adjuvants, e.g., talc, magnesium stearate, starch, lactose, gelatin, gums, and the like.

In their most advantageous form, then, the compositions of the present invention will contain a non-toxic orally-acceptable carrier in addition to the active ingredient, i.e., a compound of Formula A. Exemplary carriers are: solids — lactose, magnesium stearate, calcium stearate, starch, terra alba, dicalcium phosphate, sucrose, talc, stearic acid, gelatin, agar, pectin, acacia, or the like; liquids — elixir, solution, or suspensions in water or the like. When sugars are employed, the inert or non-plaque-forming sugars are of course preferred. The active agents of the invention can be conveniently employed in the form of such compositions containing in their broadest aspects 0.01 to 67 percent, especially 0.04 to 12.15 percent, by weight of active ingredient, although 0.1 to 5% is definitely preferred. Such formulations and oral hygiene compositions are representatively illustrated in U.S. Pat. No. 3,751,561, with or without, but preferably without, the enzyme components as therein disclosed.

A wide variety of forms suitable for orally-acceptable usage and dosages may accordingly be employed. The active ingredient and orally-acceptable carrier may, for example, in its broader aspects take the form of a gum, granule, pill, tablet, lozenge, elixir, syrup, toothpaste, mouthwash, gargle, chewable tablet, or other liquid suspension or emulsion.

The method of using the compounds of the present invention comprises exposing a tooth or teeth, or the oral cavity in which the tooth or teeth are located, to the antidental plaque activity of a compound of Formula I, preferably admixed with an orally-acceptable carrier, for example, in the form of any of the above-mentioned compositions, or filled into a capsule, for the purpose of inhibiting formation of dental plaque on the tooth, and thereby also inhibiting complications which normally result therefrom, including dental caries and periodontitis. The compounds and their fluoride salts, especially the alkyl fluorides and hydrofluorides, may be advantageously employed in any desirable form and in amounts approximating those employed in the representative compositions of the Examples hereof. Illustratively, they may be used in an amount of from about 0.1 to 100 milligrams per treatment, preferably from about 0.2 to 10 milligrams per treatment, depending upon the exact mode employed. The treatment is preferably given or undertaken a suitable number of times daily so that the daily treatment provides an effective amount of the active compound for the intended purpose, namely, inhibition of dental plaque and its resultant problems or complications as aforesaid, as already stated in the foregoing.

In addition, the active ingredients of the present invention or compositions containing the same may either be administered together with or include other active materials and/or medicaments, e.g., buffering agents, antacids, flavors anesthetics, antiseptics, surface-active agents, or the like. The compositions may take the form of impregnated dental floss mouthwashes, gargles, candies, masticable candies, lozenges, tablets, toothpowders, sprays, toothpastes, dragees, creams, salves, ointments denture cements or aids, breath purifiers, or other similar oral hygiene compositions.

The preceding formulations are representative and may be employed for incorporation of any of the pharmacologically-active compounds of the invention, but have been particularly designed to embody as active ingredient the particular compounds embodied therein, especially in the form of a pharmacologically-acceptable fluoride salt thereof, e.g., the alkyl fluoride or hydrofluoride.

Various modifications in the compounds, compositions, and methods of the invention will be apparent to one skilled in the art and may be made without departing from the spirit or scope thereof, and it is therefore to be understood that the invention is to be limited only by the scope of the appended claims.

We claim:

1. A compound of formula

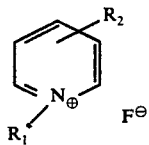

in which
$R_1$ = H or alkyl
$R_2$ = $CH_2OH$, in 2 or 3 position on the pyridyl ring, "alkyl" containing a maximum of twelve carbon atoms.

2. A compound of claim 1 selected from the group consisting of:
3-pyridylmethanol hydrofluoride,
N-dodecyl 3-pyridylmethanol fluoride, and
2-pyridylmethanol hydrofluoride.

3. Compound of claim 1 which is 3-pyridylmethanol hydrofluoride.

4. Compound of claim 1 which is N-dodecyl 3-pyridylmethanol fluoride

5. Compound of claim 1 which is 2-pyridylmethanol hydrofluoride.

6. An oral and dental hygiene composition suitable for use in the inhibition of dental plaque comprising a compound of claim 1, in an amount effective for said purpose, in association with an orally-acceptable carrier.

7. An oral and dental hygiene composition suitable for use in the inhibition of dental plaque comprising a compound of claim 2, in an amount effective for said purpose, in association with an orally-acceptable carrier.

8. An antiplaque dentifrice preparation containing, as active principle, an effective amount of a product according to claim 1.

9. An antiplaque dentifrice preparation containing, as active principle, an effective amount of product according to claim 2.

10. Orally-acceptable antiplaque composition containing an effective amount of compound of claim 1 and a bactericidal chemical compound, having properties inhibiting the formation of dental plaque.

11. An anti-plaque composition according to claim 10, characterized in that the fluorinated compound is 3-pyridylmethanol hydrofluoride and the bactericidal compound is chlorhexidine or a salt thereof.

12. A composition according to claim 10 in the form of a mouthwash, paste, topical solution, or chewing gum.

13. A composition according to claim 12, characterized in that it is in the form of a dentifrice preparation.

14. An anti-plaque composition according to claim 10, containing 0.1 to 10 percent by weight of the active principles.

15. A composition according to claim 10, having a pH which is less than 7.

16. A composition according to claim 15, characterized in that pyroglutamic acid is included as an acidifying agent.

17. An anti-plaque composition according to claim 11, in the form of a dentifrice, chewing gum, tooth gel, or mouthwash.

18. An orally-acceptable antiplaque composition according to claim 6 in the form of a mouthwash, gum paste, chewing gum, dentifrice, gel, paste, or tablet.

19. An orally-acceptable antiplaque composition according to claim 7 in the form of a mouthwash, gum paste, chewing gum, dentifrice, gel, paste, or tablet.

20. An oral and dental hygiene composition suitable for use in the inhibition of dental plaque comprising a composition of claim 10, in an amount effective for said purpose, also including an orally-acceptable carrier.

21. Method for the inhibition of dental plaque, comprising the step of contacting a tooth or the oral cavity containing said tooth with a compound of claim 1 in an amount and for a period of time effective for said purpose.

22. Method for the inhibition of dental plaque, comprising the step of contacting a tooth or the oral cavity containing said tooth with a compound of claim 2 in an amount and for a period of time effective for said purpose.

23. Method for the inhibition of dental plaque, comprising the step of contacting a tooth or the oral cavity containing said tooth with a composition of claim 10 in an amount and for a period of time effective for said purpose.

* * * * *